(12) United States Patent
Cho et al.

(10) Patent No.: US 12,399,189 B2
(45) Date of Patent: Aug. 26, 2025

(54) IMMUNOASSAY DEVICE AND IMMUNOASSAY METHOD

(71) Applicant: INVITROS CO., LTD., Seoul (KR)

(72) Inventors: Young Jun Cho, Daejeon (KR); Jae Hoon Oh, Daejeon (KR); Moon Kyoo Park, Daejeon (KR); Jeong Wook Lee, Daejeon (KR)

(73) Assignee: INVITROS CO., LTD., Seoul (KR)

( * ) Notice: Subject to any disclaimer, the term of this patent is extended or adjusted under 35 U.S.C. 154(b) by 1004 days.

(21) Appl. No.: 17/598,644

(22) PCT Filed: Mar. 20, 2020

(86) PCT No.: PCT/KR2020/003907
§ 371 (c)(1),
(2) Date: Sep. 27, 2021

(87) PCT Pub. No.: WO2020/197196
PCT Pub. Date: Oct. 1, 2020

(65) Prior Publication Data
US 2022/0163548 A1 May 26, 2022

(30) Foreign Application Priority Data
Mar. 28, 2019 (KR) .................. 10-2019-0036150

(51) Int. Cl.
*G01N 35/00* (2006.01)
*G01N 33/53* (2006.01)
(Continued)

(52) U.S. Cl.
CPC ... *G01N 35/00029* (2013.01); *G01N 33/5302* (2013.01); *G01N 35/028* (2013.01);
(Continued)

(58) Field of Classification Search
CPC ......... G01N 35/00029; G01N 33/5302; G01N 35/028; G01N 35/1009; G01N 2035/00099; G01N 2035/0418
See application file for complete search history.

(56) References Cited

U.S. PATENT DOCUMENTS 5,158,895 A    10/1992   Ashihara et al.
5,290,708 A    3/1994   Ashihara et al.
(Continued)

FOREIGN PATENT DOCUMENTS

CN    102246043 A    11/2011
CN    107024593 A    8/2017
(Continued)

OTHER PUBLICATIONS

JPH1019449A, English translation attached. (Year: 1997).*
(Continued)

*Primary Examiner* — Gregory S Emch
*Assistant Examiner* — McKenzie A Dunn
(74) *Attorney, Agent, or Firm* — ROTHWELL, FIGG, ERNST & MANBECK, P.C.

(57) ABSTRACT

The present invention relates to an immunoassay device and an immunoassay method.
According to an aspect of the present invention, an immunoassay device includes a measurement unit provided with a detection unit disposed at one side of a stage accommodating cartridges having a plurality of wells to move in a direction, in which the plurality of cartridges are arranged, and capable of measuring a state within the well disposed at the outermost side, and including a shielding plate that moves to cover an opened upper portion of the well disposed at the outermost side to block introduction of light into the well.

5 Claims, 13 Drawing Sheets

(51) Int. Cl.
  *G01N 35/02* (2006.01)
  *G01N 35/04* (2006.01)
  *G01N 35/10* (2006.01)

(52) U.S. Cl.
  CPC .................. *G01N 35/1009* (2013.01); *G01N 2035/00099* (2013.01); *G01N 2035/0418* (2013.01)

(56) References Cited

U.S. PATENT DOCUMENTS

| | | | |
|---|---|---|---|
| 5,401,465 A | 3/1995 | Smethers et al. | |
| 5,482,839 A | 1/1996 | Ashihara et al. | |
| 5,682,232 A | 10/1997 | Tajima et al. | |
| 5,773,305 A | 6/1998 | Zabetakis et al. | |
| 6,509,193 B1 | 1/2003 | Tajima | |
| 7,452,508 B2 | 11/2008 | Jacobs et al. | |
| 2001/0007770 A1 | 7/2001 | Tajima | |
| 2002/0123156 A1 | 9/2002 | Tajima | |
| 2005/0282182 A1 | 12/2005 | Tajima et al. | |
| 2006/0197955 A1 | 9/2006 | Koike | |
| 2010/0129789 A1 | 5/2010 | Self et al. | |
| 2010/0278698 A1 | 11/2010 | Tajima | |
| 2011/0009608 A1 | 1/2011 | Kim et al. | |
| 2011/0262919 A1 | 10/2011 | Tajima | |
| 2012/0122231 A1 | 5/2012 | Tajima | |
| 2012/0135394 A1 | 5/2012 | Kim et al. | |
| 2012/0140231 A1 | 6/2012 | Knox et al. | |
| 2012/0195811 A1 | 8/2012 | Nelson | |
| 2013/0121881 A1 | 5/2013 | Ishizawa et al. | |
| 2014/0048540 A1 | 2/2014 | Tajima | |
| 2014/0284223 A1 | 9/2014 | Malecha et al. | |
| 2015/0266658 A1 | 9/2015 | Tajima | |
| 2015/0309059 A1 | 10/2015 | Tajima | |
| 2016/0025722 A1 | 1/2016 | Tajima | |
| 2016/0069921 A1 | 3/2016 | Holmes et al. | |
| 2016/0169880 A1 | 6/2016 | Holmes et al. | |
| 2016/0245756 A1 | 8/2016 | Tajima | |
| 2017/0219615 A1 | 8/2017 | Matsumoto et al. | |
| 2017/0269110 A1 | 9/2017 | Horak | |
| 2017/0269114 A1 | 9/2017 | Bryant et al. | |
| 2019/0086436 A1 | 3/2019 | Lachance | |
| 2021/0132097 A1 | 5/2021 | Bryant et al. | |

FOREIGN PATENT DOCUMENTS

| | | |
|---|---|---|
| CN | 206638610 U | 11/2017 |
| CN | 109070084 A | 12/2018 |
| EP | 0725929 A1 | 8/1996 |
| EP | 0763739 B1 | 6/2005 |
| EP | 2383575 A1 | 11/2011 |
| EP | 2439537 A1 | 4/2012 |
| EP | 2600156 A1 | 6/2013 |
| EP | 2921861 A1 | 9/2015 |
| JP | H09-061341 A | 3/1997 |
| JP | H10-197449 A | 7/1998 |
| JP | 2002-055050 A | 2/2002 |
| JP | 3627593 B2 | 3/2005 |
| JP | 3682302 B2 | 8/2005 |
| JP | 3705055 B2 | 10/2005 |
| JP | 3721889 B2 | 11/2005 |
| JP | 2008-170332 A | 7/2008 |
| JP | 2008-175708 A | 7/2008 |
| JP | 2010-060537 A | 3/2010 |
| JP | 5143570 B | 2/2013 |
| JP | 2014-508034 A | 4/2014 |
| JP | 5878254 B | 3/2016 |
| KR | 10-1995-0014745 B1 | 12/1995 |
| KR | 10-0148239 B | 5/1998 |
| KR | 10-2005-0113604 A | 12/2005 |
| KR | 10-2011-0106892 A | 9/2011 |
| KR | 10-1307978 B1 | 9/2013 |
| KR | 10-2014-0031200 A | 3/2014 |
| KR | 10-1423936 B1 | 7/2014 |
| KR | 10-2015-0026003 A | 3/2015 |
| TW | 494239 B | 7/2002 |
| TW | I461690 B | 11/2014 |
| TW | I600891 B | 10/2017 |
| TW | I624543 B | 5/2018 |
| TW | I625521 B | 6/2018 |
| WO | 2015-053290 A1 | 3/2017 |
| WO | 2017-0161053 A1 | 9/2017 |

OTHER PUBLICATIONS

Examination Report issued on Oct. 11, 2023, for the European patent application No. 20776679.1, 8 pages.
The Extended Search Report for EP application No. 20776679.1 dated Mar. 9, 2022, (10 pages).
The Extended Search Report for EP application No. 20778112.1 dated Mar. 11, 2022, (8 pages).
Extended European Search Report dated Jun. 29, 2022, issued in the corresponding European Patent Application No. 20776353.3, 11 pages.
International Search Report dated Jun. 24, 2020, issued in the corresponding International Application No. PCT/KR2020/003907, 4 pages.

\* cited by examiner

IMMUNOASSAY DEVICE AND IMMUNOASSAY METHOD

CROSS-REFERENCE TO RELATED APPLICATION

This application is a 35 U.S.C. 371 National Phase Entry Application from PCT/KR2020/003907, filed on Mar. 20, 2020 and designating the United States, claims the benefit of the priority of Korean Patent Application No. 10-2019-0036150, filed on Mar. 28, 2019, all of which are hereby incorporated by references in their entirety.

TECHNICAL FIELD

The present invention relates to an immunoassay device and an immunoassay method.

BACKGROUND OF THE INVENTION

As medical and biotechnology technologies advance, tests for detecting various molecular indicators such as blood cells, genes, proteins, antigens, and pathogens in biological samples such as blood and urine are being conducted. An inspection process is generally performed by taking a sample and analyzing and observing a change occurring after allowing the collected sample with a predetermined reagent that is suitable for a desired indicator.

One of the techniques that are widely used in such an inspection process is an immunoassay method based on specific binding between antigens/antibodies.

The immunoassay method may be classified into a radio-immunoassay (RIA), in which a signal is detected using radioactive isotopes, an enzyme-linked immunosorbent assay (ELISA) or enzyme immunoassay (EIA) that uses signal amplification by enzymes, a fluorescence antibody technique (FA) using fluorescence, chemiluminescence immunoassay (CLIA) using chemiluminescence, and the like, according to a detection principle and method thereof. In addition, the immunoassay method may be variously classified according to a method of using a marking material or types of substrates.

An immunoassay device for implementing the immunoassay method according to the related art has a disadvantage that it is inefficient to test various samples because a cartridge having the same reaction method is disposed on one stage.

In addition, the immunoassay device according to the related art has a disadvantage that it takes a long time to measure a state of a final reaction solution.

Also, in the immunoassay device according to the related art, magnetic particles are discharged to the outside of a tip to cause a risk of incorrect immunity testing.

BRIEF SUMMARY OF THE INVENTION

Embodiments of the present invention are proposed to solve the above problems, and the present invention is to provide an immunoassay device and an immunoassay method, which are capable of performing various reaction methods on one state.

In addition, the present invention is to provide an immunoassay device and an immunoassay method which are capable of reducing a time taken to measure a state of a final reaction solution.

In addition, the present invention is to provide an immunoassay device and an immunoassay method, which are capable of performing a more precise reaction inspection because magnetic particles are held in a tip a process of implementing a reaction method.

In addition, the present invention is to provide an immunoassay device and an immunoassay method, in which reaction and inspection of a sample and a reagent occurs in one small device.

An immunoassay device according to an embodiment of the present invention includes: a stage which is capable of accommodating a plurality of cartridges having a plurality of wells that are opened upward and capable of surrounding a circumference of the well disposed at the outermost side of the cartridges; a solution transfer unit including a plurality of tips, which are movable relative to the stages, are disposed to correspond to positions of the cartridge, and suction a solution stored in the well or discharge the suctioned solution from the well; and a measurement unit disposed at one side of the stages to move in a direction in which the plurality of cartridges are arranged, provided with a detection unit that is capable of measuring a state within the well disposed at the outermost side, and including a shielding plate that moves to cover an opened upper portion of the well disposed at the outermost side to block introduction of light into the well.

In the immunoassay device according to an embodiment of the present invention, a first hole may be provided in one side surface of the stage that surrounds the circumference of the well, which is disposed at the outermost side, of the cartridges so as to measure a state of the solution, the detection unit may be provided on one side surface of the measurement unit; and when the detection unit is disposed on the side surface of the well disposed at the outermost side to measure the state of the solution, the light incident into the well through the first hole may be blocked.

In the immunoassay device according to an embodiment of the present invention, a second hole through which an end of the tip is introduced into an upper portion of the well disposed at the outermost side may be provided in the shielding plate, the second hole may have a size less than that of an upper hole of the well disposed at the outermost side, and when the tip is introduced into the well disposed at the outermost side, the light incident into the well through the second hole may be blocked.

In the immunoassay device according to an embodiment of the present invention, the detection unit and a second hole formed in the shielding plate may be provided in plurality to measure states of the solutions stored in the plurality of wells disposed at the outermost side at the same time.

In the immunoassay device according to an embodiment of the present invention, an injection of the solution from the tip into the well disposed at the outermost side and the measurement of the state of the solution by the detection unit may be performed at the same time.

In the immunoassay device according to an embodiment of the present invention, as the solution stored in the tip is injected into the well disposed at the outermost side, a luminant of the solution may emit light, and the detection unit may measure the emitted light.

In the immunoassay device according to an embodiment of the present invention, a light emission time of the luminant may be within 10 seconds, and the measurement of the state of the solution by the detection unit may be performed within 10 seconds.

In the immunoassay device according to an embodiment of the present invention, the solution transfer unit may include a magnetic force applying part that is capable of applying magnetic force toward the tip, and when the solution stored in the tip is injected into the well disposed at the outermost side, as the magnetic force applying part approaches the tip, magnetic particles may be held inside the tip.

The immunoassay device according to an embodiment of the present invention may further include a measurement unit driving part that is capable of driving the measurement unit in at least one direction, wherein the measurement unit may be reciprocated along the wells, which are disposed at the outermost side, of the plurality of cartridges.

An immunoassay method according to an embodiment of the present invention includes: a step in which a tip moving along a cartridge and storing a solution containing magnetic particle conjugate is disposed above a well disposed at the outermost side; a step in which a measurement unit moves in one direction so as to be disposed on a side surface of the well disposed at the outermost side, and a shielding plate covers an upper portion of the well disposed at the outermost side; a step in which the solution stored in the tip is injected to the inside of the well; and a step of measuring a state of the solution by a detection unit while injecting the solution.

In the immunoassay method according to an embodiment of the present invention, the step in which the measurement unit moves in the one direction so as to be disposed on the side surface of the well disposed at the outermost side may include a step of blocking light incident into the well through a first hole provided in one side surface of the stage, which is capable of surrounding a circumference of the well disposed at the outermost side.

In the immunoassay method according to an embodiment of the present invention, the step in which the tip descends into the well disposed at the outermost side may include a step of blocking the light incident into the well through a hole formed in an upper portion of the well disposed at the outermost side.

Advantageous Effects

In the immunoassay device and the immunoassay method according to the embodiments of the present invention, the various reaction methods may be performed on one stage.

Also, the time taken to measure the state of the final reaction solution may be reduced.

Also, in the process of implementing the reaction method, the magnetic particles may be held in the tip to perform the more precise immunoassay.

Also, the reaction and inspection of the sample and the reagent may occur in one small device.

DETAILED DESCRIPTION OF THE INVENTION

Hereinafter, specific embodiments of the present invention will be described in detail with reference to the drawings.

Moreover, detailed descriptions related to well-known functions or configurations will be ruled out in order not to unnecessarily obscure subject matters of the present invention.

Figure 1:
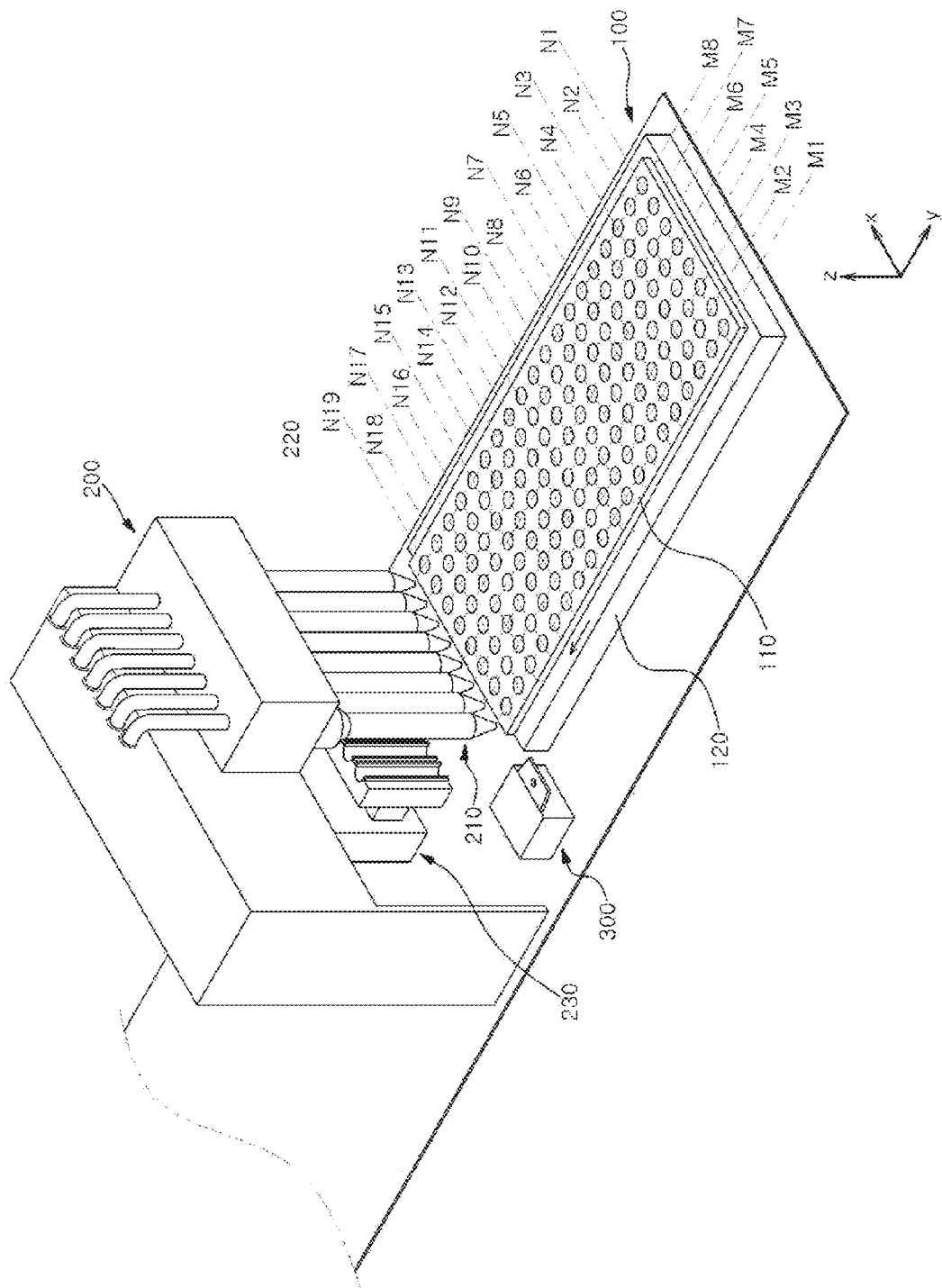
FIG. 1 is a schematic perspective view illustrating a configuration of an immunoassay device according to an embodiment of the present invention.
Figure 2:
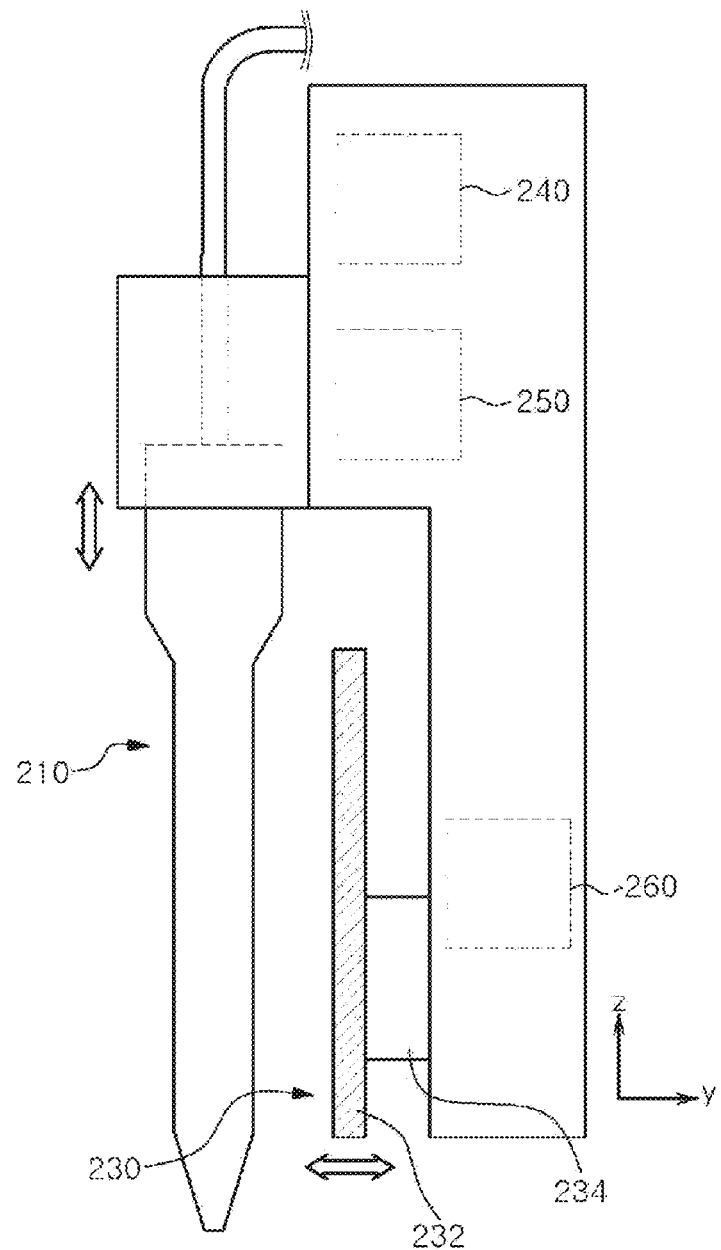
FIG. 2 is a schematic view illustrating a side surface of a solution transfer unit of FIG. 1.
Figure 3:
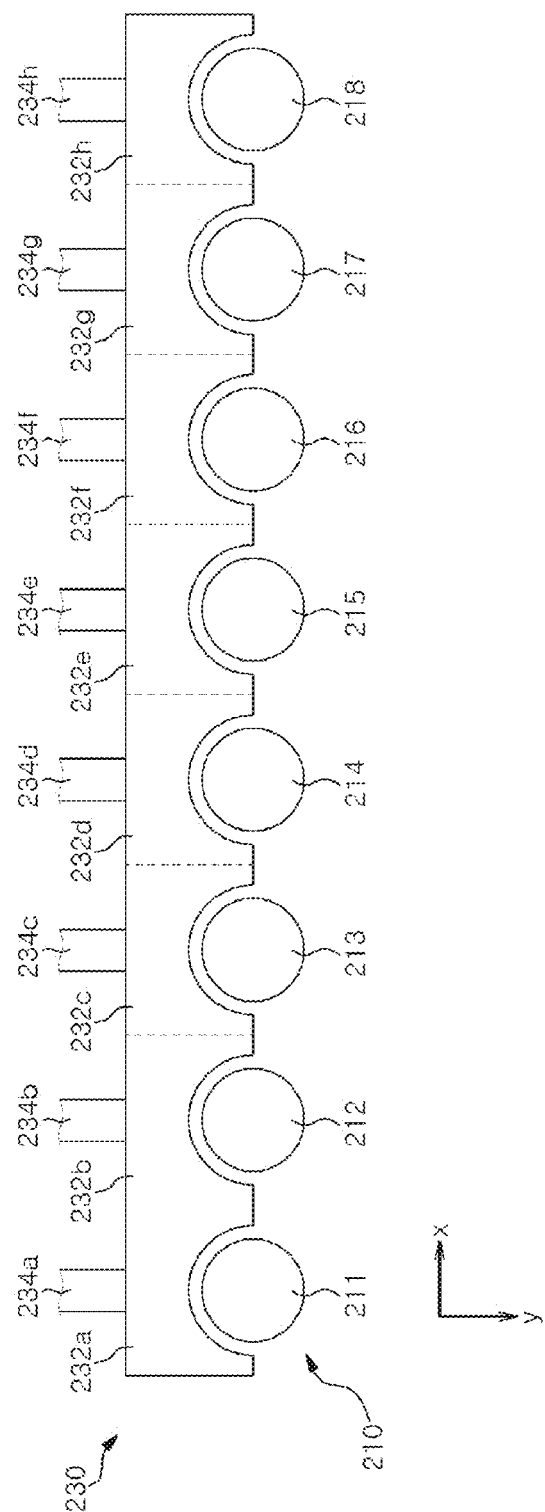
FIG. 3 is a schematic cross-sectional view illustrating a magnetic force applying part of FIG. 1.
Figure 4:
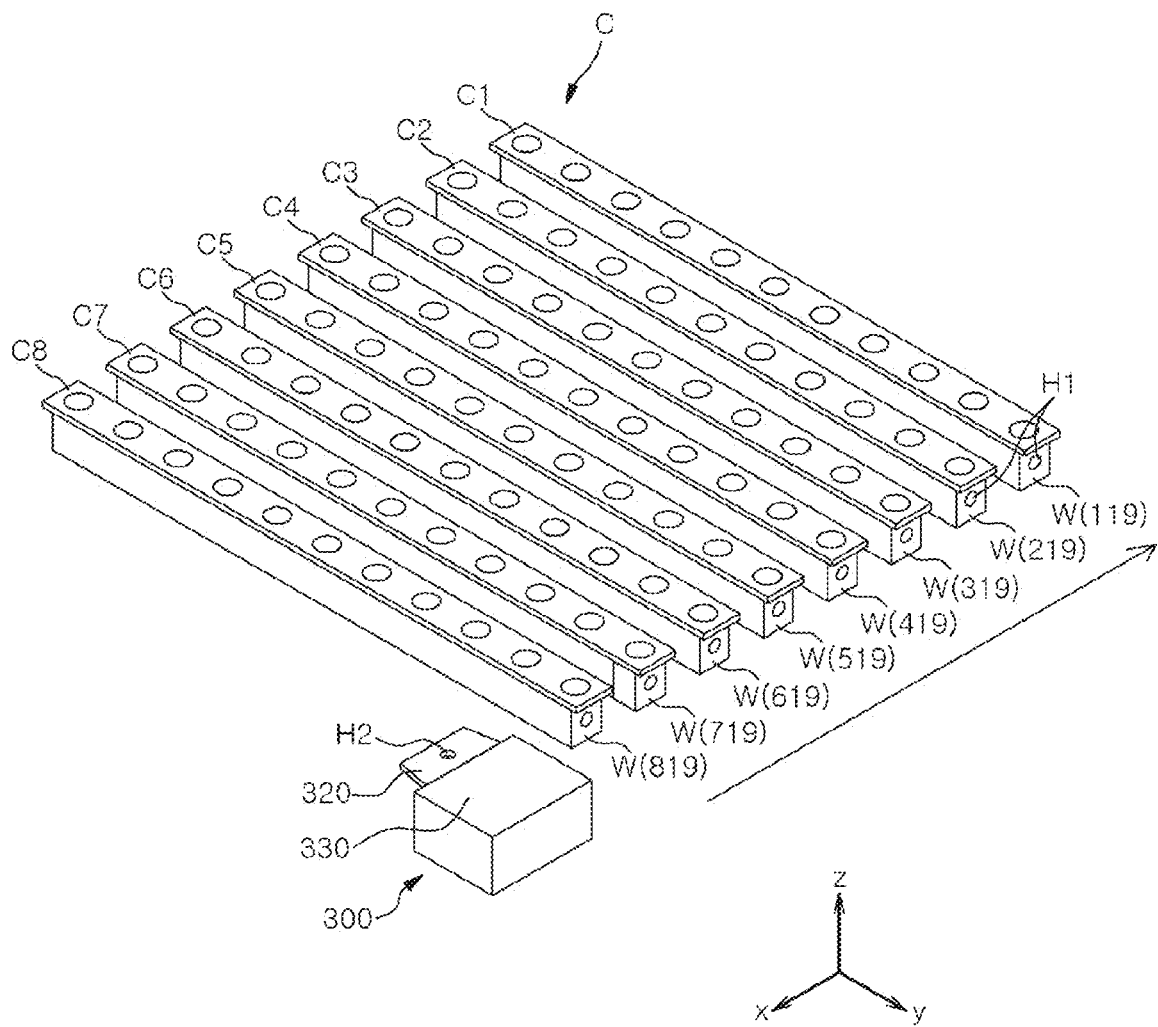
FIG. 4 is a schematic view illustrating an operation path of a measurement unit of FIG. 1.
Figure 5:
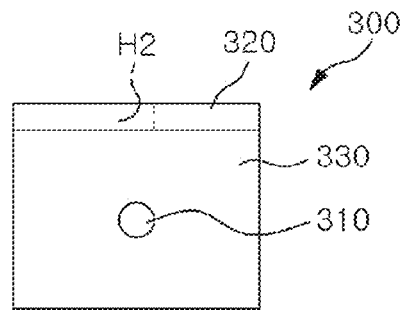
FIG. 5 is a view illustrating a front surface, a side surface, and a top surface of the measurement unit of FIG. 1.
Figure 5:
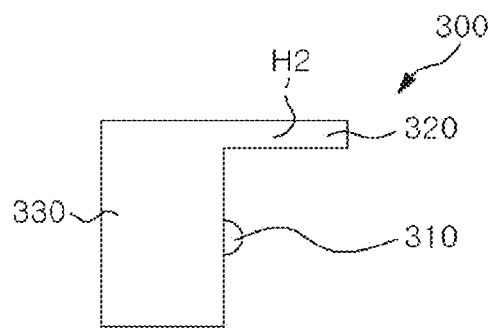
Figure 5:
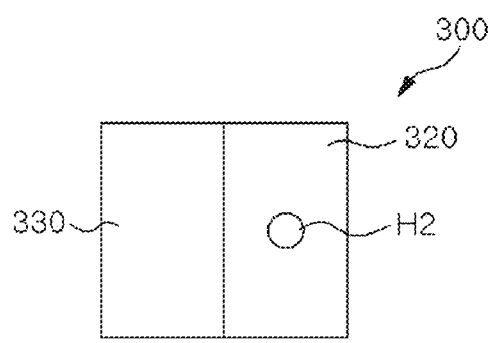
Figure 7:
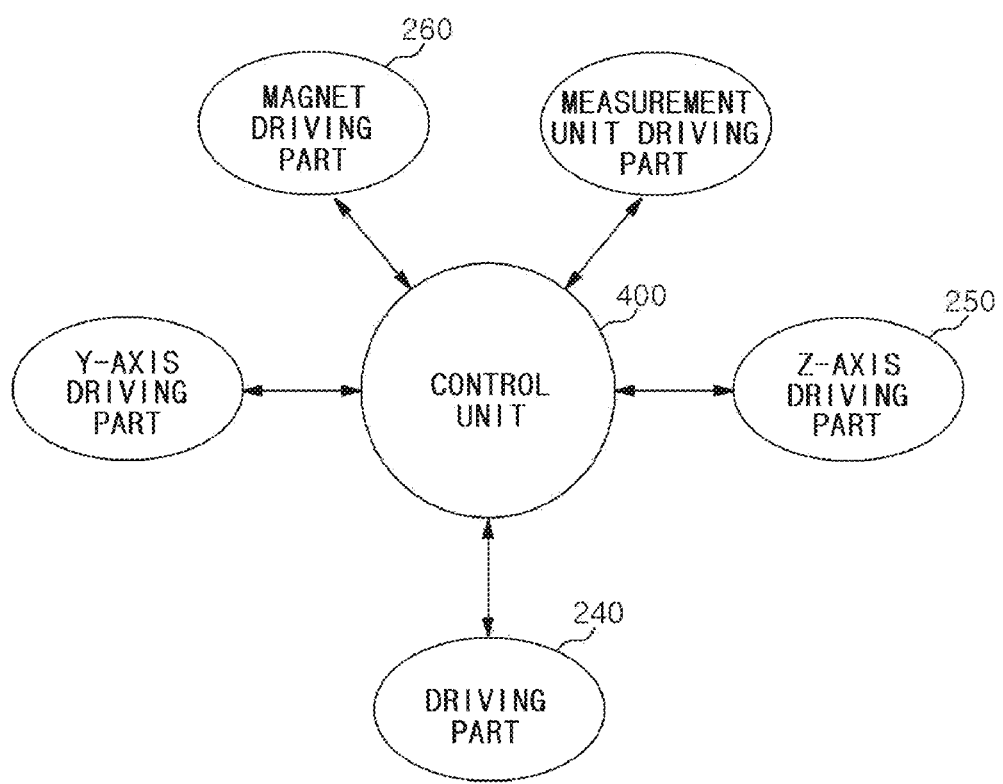
FIG. 7 is a block diagram of various driving units associated with a control unit of FIG. 1.

FIG. 1 is a schematic perspective view illustrating a configuration of an immunoassay device according to an embodiment of the present invention, FIG. 2 is a schematic view illustrating a side surface of a solution transfer unit of FIG. 1, FIG. 3 is a schematic cross-sectional view illustrating a magnetic force applying part of FIG. 1, FIG. 4 is a schematic view illustrating an operation path of a measurement unit of FIG. 1, FIG. 5 is a view illustrating a front surface, a side surface, and a top surface of the measurement unit of FIG. 1, and FIG. 7 is a block diagram of various driving units associated with a control unit of FIG. 1.

Referring to FIGS. 1 to 5 and 7, an immunoassay device 10 according to an embodiment of the present invention may include a stage 100 capable of accommodating a cartridge C, a solution transfer unit 200 including a plurality of tips 210 that is capable of suctioning a solution stored in the cartridge C or discharging the solution suctioned from the cartridge C, a measurement unit 300 measuring a state of the solution stored in the cartridge C, and a control unit 400 controlling the solution transfer unit so that the stage 100 and the solution transfer unit 200 move relative to each other, and at least a portion of the tips 210 suctions the same content from the plurality of cartridges at the same time or discharges the same content to the plurality of cartridges at the same time. Here, the content may refer to a solution in the tip 210 or a solution in a well W in each of steps as the solution transfer unit 200 and the stages relatively move to perform each of the steps for reaction.

The cartridge C according to an embodiment of the present invention stores reagents for detection and/or analysis of an analyte contained in a sample. The term "sample" used in this embodiment refers to a compound or composition to be analyzed, which contains the analyte, and the sample that is capable of being used in the present invention may be a liquid phase or liquid-like fluidic material. In an embodiment of the present invention, the sample may be a biological sample, i.e., be a bio-derived component such as whole blood, plasma, serum, urine, saliva, manure, and cell extract. In this embodiment, a left-right direction is described in a Y-axis direction, and a vertical direction is described in a Z-axis direction based on FIG. 2. An X-axis direction is described in a direction perpendicular to the Y-axis direction and the Z-axis direction. In addition, the directional setting may be merely an example, and the direction indicated by each axis direction may be set differently according to an embodiment.

The stage 100 includes a cartridge accommodation part 110 that is capable of accommodating the plurality of cartridges C having the plurality of wells W, and a Y-axis guide part 120 that is capable of guiding movement of the cartridge accommodation part 110.

The cartridge accommodation part 110 may be provided in a planar shape extending in the X-axis and Y-axis directions and may include a plurality of grooves that are capable of accommodating the wells W of the cartridges.

The grooves formed in the cartridge accommodation part 110 may be arranged in an M×N matrix. Here, M and N are arbitrary natural numbers, M rows are parallel to the Y-axis, and N columns are parallel to the X-axis. For example, when arranged in an 8×19 matrix as described in the embodiment of the present invention, the cartridge accommodation part 110 may include 152 grooves. However, the number of M rows and N columns is merely an example and thus is not limited thereto.

One cartridge C may be accommodated in one row M of the cartridge accommodation part 110. For example, as described in the embodiment of the present invention, eight cartridges may be disposed in the cartridge accommodation part 100 having eight rows M1 to M8.

Reagents having different reaction methods may be stored in each of the cartridges C. Thus, various immunoassays may be performed on one stage 100, and detailed description thereof will be described later.

The cartridge accommodation part 110 may reciprocate in the Y-axis direction. As the cartridge accommodation part 110 in which the cartridge C is disposed moves in the Y-axis direction, and the solution transfer unit 200 to be described later moves in the Z-axis, the solution stored in the well W of the cartridge may be suctioned into the plurality of tips 210, and the solution suctioned from the well W may be discharged.

Also, a Y-axis driving part (not shown) that is capable of allowing the cartridge accommodation part 110 to move in the Y-axis direction may be provided.

A lower portion of the cartridge accommodation part 110 may include a heating block (not shown) capable of being adjusted in temperature to cultivate the solution (a mixture of the sample and the reagent) stored in the well W. Here, the heating block may be disposed to surround a lower end of each of the wells W, and it is possible to adjust the temperature for the cultivation of the solution in the well.

The Y-axis guide unit 120 may guide the cartridge accommodation part 110 so as to be reciprocated in the Y-axis direction. Also, the Y-axis guide unit 120 may surround the outside of the heating block and block external light from being introduced into the cartridge C.

The solution transfer unit 200 may include the plurality of tips 210, a punching part (not shown) disposed in front of the tips 210 to punch a film of the well W, and a magnetic force applying part 230 disposed behind the tips 210 to fix magnetic particles suctioned into the tips 210. Here, the front side may be a direction in which the first well in the Y-axis direction is disposed.

Also, the solution transfer unit 200 may include a driving part 240 capable of independently applying a pressure to each of the plurality of tips 210, a Z-axis driving part 250 capable of allowing the plurality of tips 210 and the punching part to move in the Z direction, and a magnet driving part 260 capable of allowing the magnetic force applying part 230 to move in the Y-axis direction.

The plurality of tips 210 may suction the solution stored in the well W or discharge the solution suctioned from the well W. For example, the plurality of tips 210 may be provided in eight (first tips 211 to eighth tips 218), which respectively suction the stored in each of the wells W of the cartridges disposed in the first row M1 to eight row M8 or discharge the solution suctioned from the wells W.

The plurality of tips 210 may be disposed in the same row to move along the same row. For example, the eight tips 211 to 218 may move along the same column N1 to N19 and then be introduced into the respective wells of the cartridge C disposed in the same column N1 to N19 to move. As described above, the plurality of tips 210 may move along the same column N1 to N19 to adjust an arrangement of the column of the wells W of each of the cartridges C so that a plurality of reaction methods are executed at the same time. This will be described below in detail.

Also, each of the plurality of tips 210 may independently suction or discharge the solution by the driving part 240, and detailed descriptions thereof will be described later. The plurality of tips 210 may be separated from the solution transfer unit 200 and may be mounted on the solution transfer unit 200 after the punching part punches each of the wells W of the cartridge C.

The punching part (not shown) may be a constituent that punches the well W of the cartridge C to form a hole and may have an end having a pointed shape. Also, the punching part (not shown) may have a number corresponding to the number of cartridges C. For example, the punching part (not shown) may be provided in eight to correspond to the number of cartridges C disposed in the first to eight rows M1 to M8.

When the tip 210 is separated from the solution transfer unit 200, the punching part may have a length at which the only the punching part (not shown) reaches the film of the well W to punch the film, and when the tip 210 is mounted on the solution transfer unit 200, the punching part may have a length at which the punching part (not shown) does not reach the well W. That is, the length of the tip 210 may be provided longer than that of the punching part (not shown).

Also, the plurality of tips 210 and the punching part (not shown) may move in the vertical direction (Z-axis direction). Here, movement of the plurality of tips 210 and the punching part (not shown) in the Z-axis direction may be performed depending on each other, but is not limited thereto, and movement of the plurality of tips 210 and the punching part (not shown) in the Z-axis direction may be independent.

The magnetic force applying part 230 may be disposed behind the plurality of tips 210 (a direction that is away from the first well of the cartridge in the Y-axis) to move toward the tips, thereby fixing the magnetic particles inside the tips 210.

The magnetic force applying part 230 may include a magnet 232 movable in a direction toward or away from the tip 210 from one side surface of the tip 210 and a magnet moving part 234 for allowing the magnet 232 to move in one direction.

The magnet 232 may be a shape (a shape that is mutually fitted with) corresponding to a circumference of the tip 210. For example, when the tip 210 is viewed from the top side, if the tip 210 has a circular shape, the magnet 232 may be a concave shape that is fitted with the tip (see FIG. 3).

Since the magnet 232 and the tip 210 are fitted with respect to each other, magnetic force applied to the magnetic particles inside the tip 210 may be constantly adjusted. Also, when viewed from the top side of the tip 210, the magnet 232 may wrap more than half around the tip 210.

Also, when viewed from one side of the tip 210, a length of the magnet 232 (Z-axis direction) may be more than half of the length of the tip 210. For example, the length of the magnet 232 may be 80% or more of the length of the tip 210. Since the magnet 232 has the above-described length, the magnetic particles may be fixed on a large area inside the chip 210.

The magnet 232 may be integrally formed. Also, the magnets 232 may be provided in a plurality along the X-axis direction to independently move toward or be away from the plurality of tips 210. For example, when the eight tips 211 to 218 are provided, eight magnets 232a to 232h corresponding to the eight tips 211 to 218 may be provided. In this case, eight magnet moving parts 234a to 234h capable of independently driving each of the magnets 232a to 232h may be provided.

Also, the magnetic force applying part 230 may be an electromagnet, in which the magnetic force is changed in magnitude, instead of the permanent magnet. In this case, the magnetic particles may be fixed inside the tip 210 by changing only the magnitude of the magnetic force without moving toward the tip 210 or without using a moving device.

A process in which the magnetic particles are held inside the tip 210 by the magnetic force applying part 230 will be described as follows.

First, a fixture solution containing magnetic particles is introduced into the tip 210 by a suction pressure of the driving part 240. Thereafter, a cleaning solution stored in the well W of the cartridge C is introduced into the tip 210. Thereafter, a pneumatic pressure of the driving part 230 is adjusted to generate a flow inside the tip. Then, the magnetic force applying part 230 moves in the direction toward the tip 210 to fix the magnetic particles inside the tip 210. Then, the solution containing impurities may be discharged to the well W, and thus, the magnetic particles may be fixed inside the tip. As described above, precision of the reaction may increase by holding the magnetic particles inside the tip 210.

The driving part 240 may independently apply a pressure to the plurality of tips 210. For example, the driving part 240 may be a pump provided with pneumatic pressure.

The driving part 240 may not only provide a pressure for allowing each of the tips 210 to suction or discharge the solution by using the pneumatic pressure, but also cause mixing (flow of the solution) of the solution inside the tip 210. For example, the driving part 240 may adjust the pressure inside the tip 210 by suctioning air inside the tip 210 or discharging air toward the inside of the tip 210. Due to the change in pressure inside the tip 210, the solution inside the tip 210 may flow in the vertical direction, and thus the mixing of the solution may occur inside the tip 210.

The driving part 240 may independently apply a pressure to each of the tips 210. Particularly, when each of the tips 210 is introduced into the empty well of the cartridge C, the driving part 240 may not provide a pressure to the tip 210 introduced into the empty well. For example, when the first tip 211 is introduced into the well W16 disposed in the sixth column N6 of the first cartridge C1, the driving part 240 may provide a pressure for suctioning a conjugate solution stored in the well W16, and simultaneously, when the third tip 213 is introduced into the well W36 disposed in the sixth column N6 of the third cartridge C3, since no solution is stored in the well W36, a pressure may not be applied to the third tip 213. This illustrates only two tips 211 and 213 of the eight tips 211 to 218, and thus, the remaining tips 212 and 214 to 218 may operate in the same principle.

The measurement unit 300 may be movable along one side (for example, the X-axis direction) of the stage 100 may measure a state of a solution from the tip 210 to any one well W of the cartridge 100. Also, a measurement unit driving part (not shown) that is capable of allowing the measurement unit 300 to move in the X-axis direction may be provided.

The measurement unit 300 may include a detection unit 310 that is capable of measuring an internal state of the well W disposed at the outermost side of each of the cartridges C and a shielding plate 320 that shields an opened upper portion of the well W disposed at the outermost side to block introduction of light into the well W.

The measurement unit 300 may be movable along one side of the stage 100 and measure a state of the well disposed at the outermost side of each of the cartridges C. Also, the measurement unit 300 may be an optical reading module that optically analyzes a reaction result of the sample and the reagent.

The measurement unit 300 may be disposed on a side surface of the well W disposed at the outermost side to complete the measurement n a short time when the solution is injected from the tip 210 to the well W disposed at the outermost side. For example, the measurement of the state of the solution by the measurement unit 300 may be performed within 20 seconds.

Also, the measurement unit 300 of the present invention may be provided in a flash type, and a darkroom may be required to measure light emitted from a luminant of the solution.

In this embodiment, for the condition of the darkroom, a circumference of the well W disposed at the outermost side of each of the cartridges C may be surrounded by a block (or the heating block), and also, the detection unit 310 and the shielding plate 320 may be used for the circumference of the well W.

The detection unit 310 may measure a state within the solution of the well W disposed at the outermost side (for example, the detection unit 310 may be any known measurement unit such as a camera), and the detection unit may have an outer appearance that serves to block the introduction of light into the well W disposed at the outermost side.

For example, a first hole H1 may be provided in one side surface of the stage 100 capable of surrounding the circumference of the well W disposed at the outermost side of the cartridge C, and the detection unit 310 may be introduced into the first hole H1 to block light introduced from the first hole H1.

Here, a shape and size of the detection unit 310 may be provided to correspond to those of the first hole H1. For example, when the first hole H1 has a rectangular shape, the shape of the detection unit 310 may also have a rectangular shape.

The shielding plate 320 may function to block the introduction of light to an upper portion of the well W disposed at the outermost side. Also, the shielding plate 320 may extend from an upper edge of a main body 330 of the measurement unit to block the upper portion of the well W disposed at the outermost side. However, a second hole H2 through which an end of the tip 210 is introduced into the well W disposed at the outermost side may be provided in the shielding plate 320.

The second hole H2 may be formed less than an upper hole of the well W disposed at the outermost side, and when the tip 210 is introduced into the well W disposed at the outermost side, the light introduced into the well through the second hole H2 may be blocked.

Also, when the detection unit 310 has a convex shape protruding in the Y-axis direction, the measurement unit 300 may move in the X-axis direction and be disposed in the well W disposed at the outermost side, and then move by the convex shape protruding in the Y-axis direction.

The control unit 400 may control various driving parts for driving the invention. For example, the control unit 400 may control a Y-axis driving part (not shown) capable of allowing the cartridge accommodation part 110 to move in the Y-axis direction, a driving part 240 that is capable of independently applying a pressure to each of the plurality of tips 210, a Z-axis driving part 250 capable of allowing the plurality of tips 210 and the punching part (not shown) to move in the Z-axis direction, a magnet driving part 230 capable of allowing the magnetic force applying part 230 to move in the Y-axis direction, and a measurement unit driving part (not shown) capable of allowing the measurement unit 300 to move in the X-axis direction and the Y-axis direction.

The control unit 400 may control the tips so that at least the other tip stands by above the empty well while at least one tip of the plurality of tips suctions the solution stored in the well and discharge the suctioned solution from the well.

Figure 6:
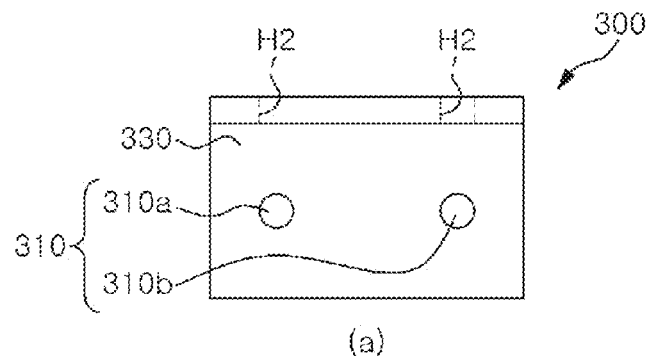
FIG. 6 is a view illustrating a measurement unit of FIG. 5 according to another embodiment.
Figure 6:
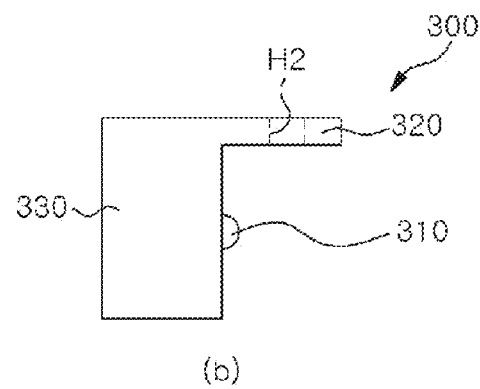
Figure 6:
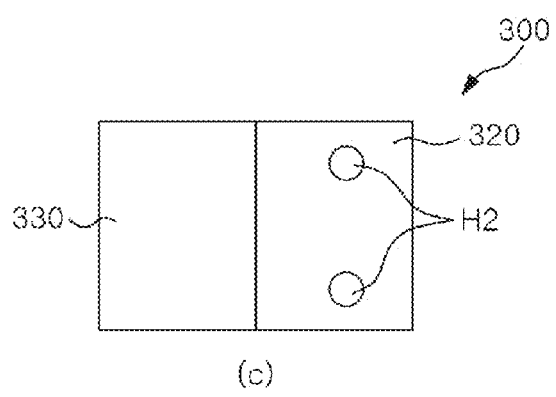

FIG. 6 is a view illustrating a measurement unit of FIG. 5 according to another embodiment.

Referring to FIG. 6, a plurality of second holes H2 formed in the detection unit 310 and the shielding plate 320 may be provided to simultaneously measure internal states of the solutions of the plurality of wells disposed at the outermost side. Here, a distance between the plurality of detection unit 310 and the plurality of second holes H2 may be the same as a distance between a plurality of tips 210.

In this case, the solution injection from the tip 210 into the well W disposed at the outermost side and the measurement of the state of the solution of the detection unit 310 may occur at the same time.

Figure 8:
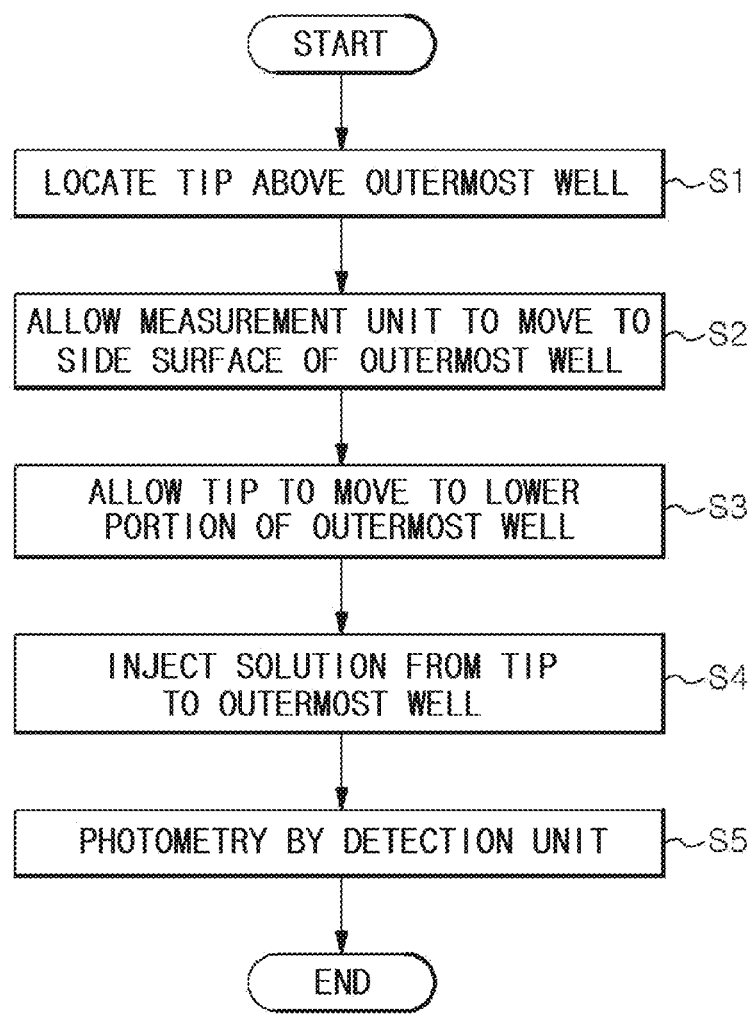
FIG. 8 is a flowchart illustrating a process of measuring a state of a solution by the measurement unit of FIG. 1.

FIG. 8 is a flowchart illustrating a process of measuring a state of a solution by the measurement unit of FIG. 1.

Referring to FIG. 8, a process of measuring an internal state of a well W disposed at the outermost side of each of cartridges C by a measurement unit 300 will be described as follows.

First, while the cartridge moves, a tip 210 in which a solution containing a luminant, magnetic particles, and a pre-trigger is stored is disposed above the well W disposed at the outermost side (S1).

Thereafter, a measurement unit 300 moves in the X-axis direction and is disposed on a side surface of a well W119 disposed at the first outermost side (S2). Here, light introduced from the side surface toward the well W119 disposed at the outermost side is blocked, and a shielding plate 320 covers an upper portion of the well W119 disposed at the outermost side.

Thereafter, a tip 210 descends into the well W119 disposed at the outermost side (S3). Here, light introduced from an upper side toward the well W119 disposed at the outermost side is blocked (S3).

Thereafter, a luminant of the solutions stored in the tip 210 is injected toward the well W119 disposed at the outermost side (S4). Here, a magnetic force applying part 230 approaches the tip 210, and thus, the magnetic particles may be held inside the tip 210.

Thereafter, alternatively, a detection unit 310 may detect the luminant while injecting the solution to complete the measurement of the state of the solution injected from one tip 211 (S5).

A measurement unit 300 may move to the X-axis, and then, the above-described process may be repeated to measure a state of solutions of the remaining wells W219 to W819 disposed at the outermost side.

Figure 9:
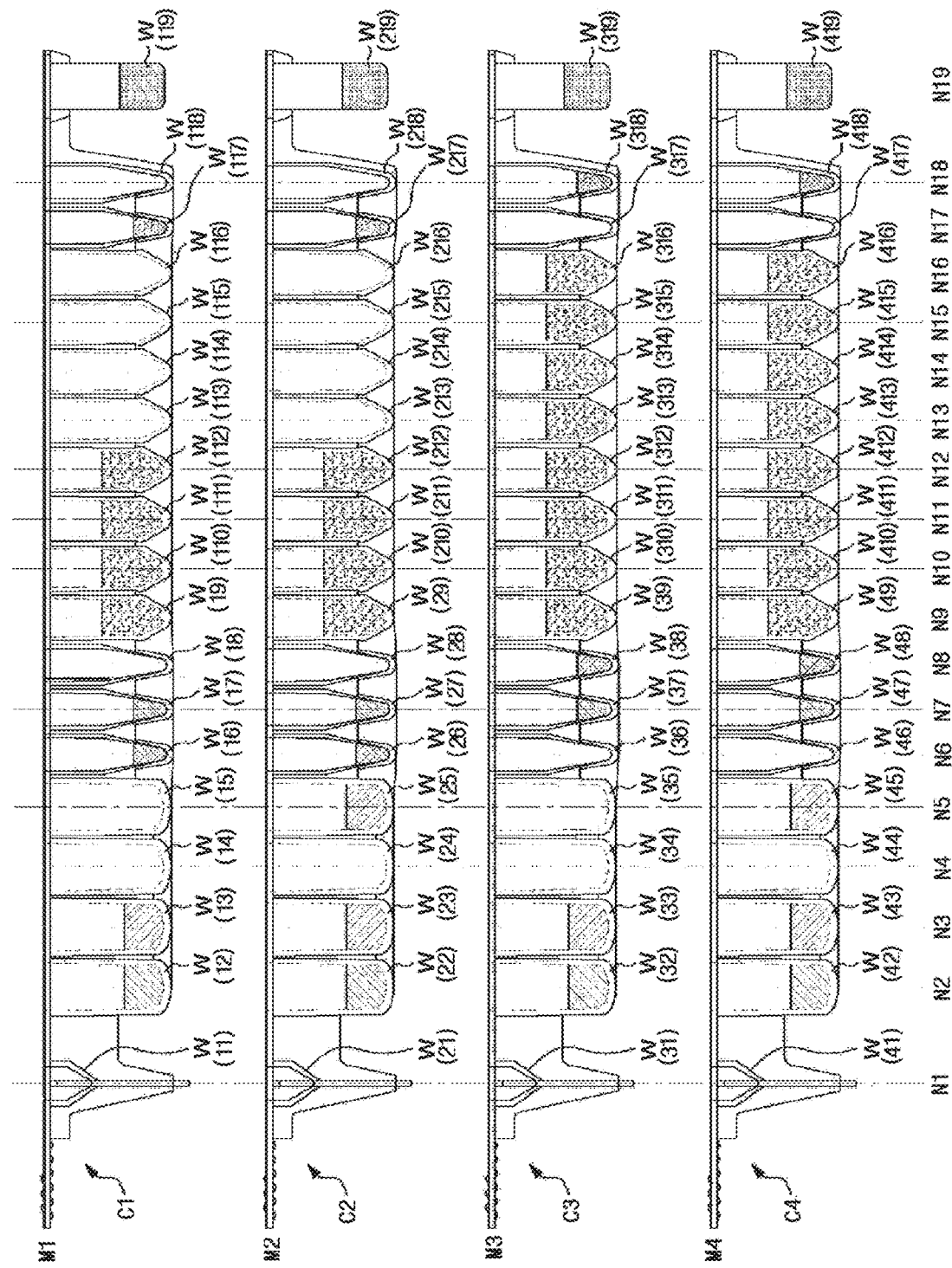
FIG. 9 is a schematic view of a plurality of cartridges of FIG. 1 and a reagent stored in each of wells of the cartridges.
Figure 10:
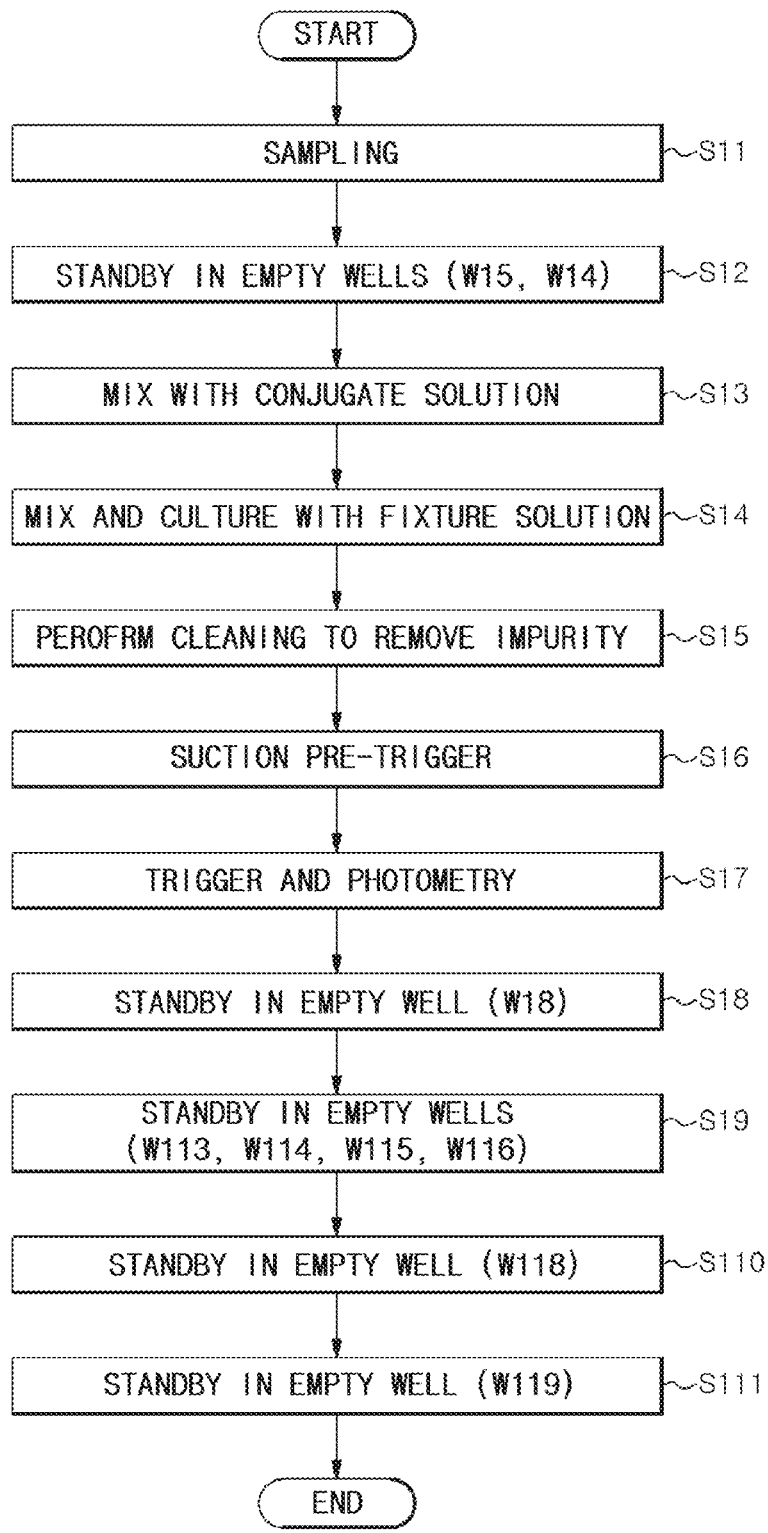
FIG. 10 is a flowchart illustrating a process of a first step assay using a first cartridge of FIG. 9.
Figure 11:
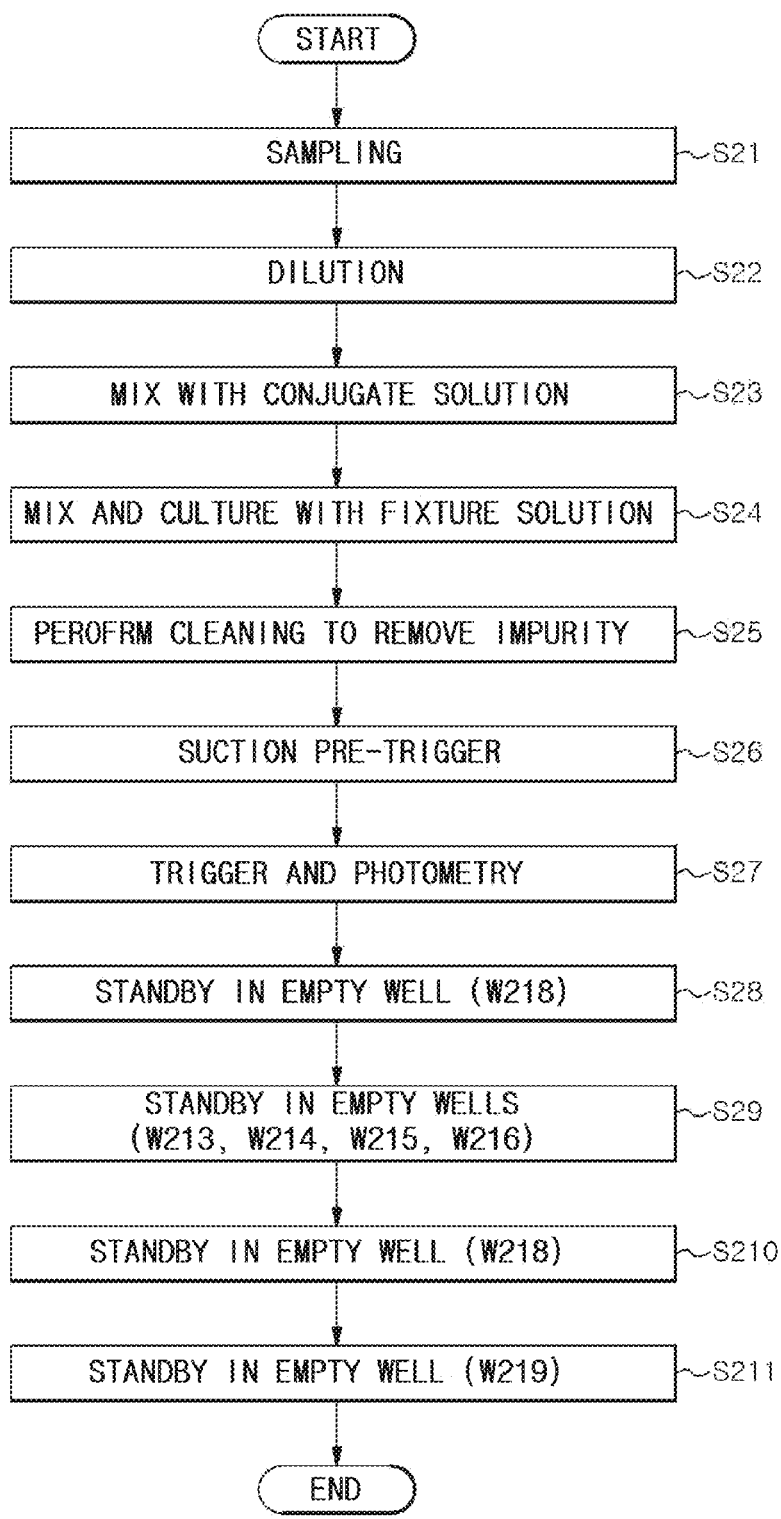
FIG. 11 is a flowchart illustrating a process of a first step dilution assay using a second cartridge of FIG. 9.
Figure 12:
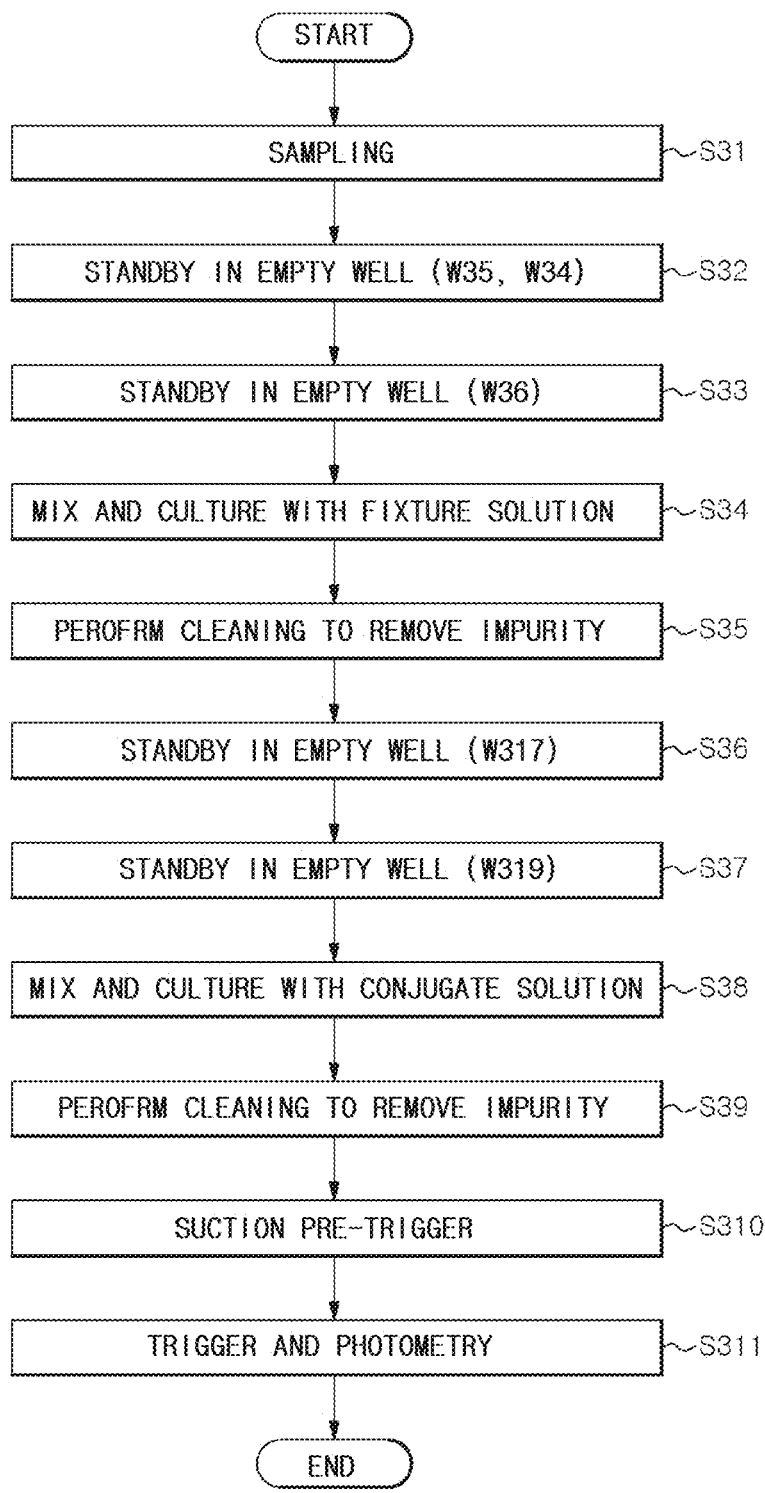
FIG. 12 is a flowchart illustrating a process of a second step assay using a third cartridge of FIG. 9.
Figure 13:
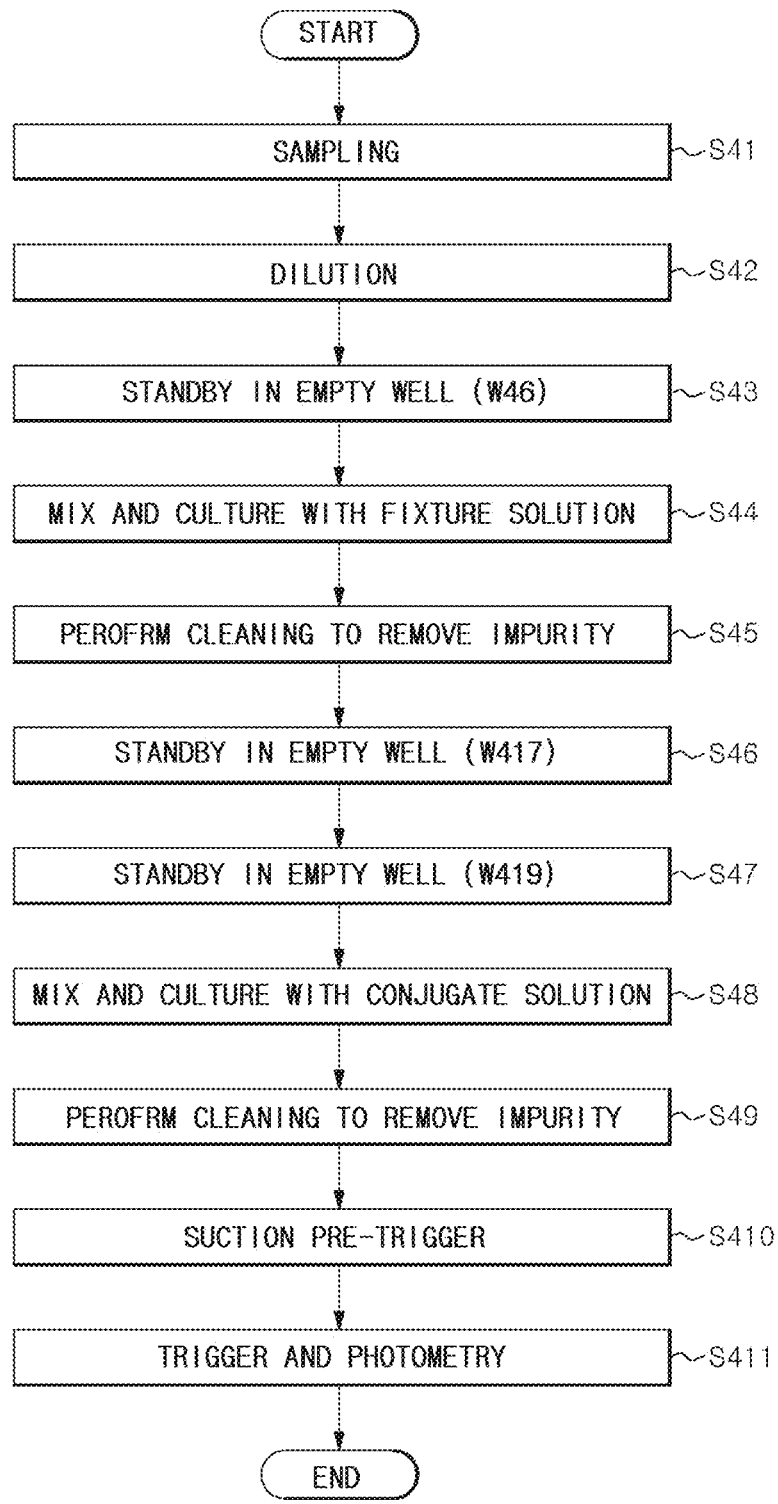
FIG. 13 is a flowchart illustrating a process of a second step dilution assay using a fourth cartridge of FIG. 9.

FIG. 9 is a schematic view of a plurality of cartridges of FIG. 1 and a reagent stored in each of wells of the cartridges, FIG. 10 is a flowchart illustrating a process of a first step assay using a first cartridge of FIG. 9, FIG. 11 is a flowchart illustrating a process of a first step dilution assay using a second cartridge of FIG. 9, FIG. 12 is a flowchart illustrating a process of a second step assay using a third cartridge of FIG. 9, and FIG. 13 is a flowchart illustrating a process of a second step dilution assay using a fourth cartridge of FIG. 9.

Referring to FIGS. 9 to 13, each of cartridges C disposed in each of rows M1 to M8 of a cartridge accommodation part 110 may store reagents having different reaction methods. Accordingly, the cartridge C having a plurality of reaction methods may be disposed on one stage 100 to perform various immunoassays.

For example, four cartridges C1 to C4 arranged in the rows M1 to M4 of the cartridge accommodation part 110 are disposed. A reagent for implementing first reaction is stored in the first cartridge C1, a reagent for implementing second reaction is stored in the second cartridge C2, a reagent for implementing third reaction is stored in the third cartridge C3, and a reagent for implementing fourth reaction is stored in the fourth cartridge C4. The plurality of reaction methods (the first to fourth reaction methods) may be implemented in a single procedure by relative movement of a solution transfer unit 200 and a cartridge accommodation part 110.

In this embodiment, the first reaction, the second reaction, the third reaction, and the fourth reaction will be described as a first step assay, a first step dilution assay, a second step assay, and a second step dilution assay as examples, respectively. However, the first to fourth reactions are not limited thereto and may include all known reaction methods for the immunoassay.

The first cartridge C1 is a container containing a reagent for implementing the first step assay, the second cartridge C2 is a container containing a reagent for implementing a first step dilution assay, the third cartridge C3 is a container containing a reagent for implementing the third step assay, and the fourth cartridge C4 is a container containing a reagent for implementing a fourth step dilution assay.

A diluent that is capable of dilutes the sample, a conjugate solution containing a luminant, a fixture solution containing magnetic particles, a cleaning solution, and a pre-trigger that is capable of absorbing the luminant to provide side light may be stored in each of the wells W of the first to fourth cartridges C1 to C4. Also, each of the cartridges C1 to C4 may include an additional empty well W in addition to the empty well W for injecting the sample. Also, each of the cartridges C1 to C4 may optionally include a piercer rincer and a piercer cleaner, which are capable of removing foreign substances of a punching part (not shown).

Also, the empty well W and the well W containing each of the reagents may be arranged so that the first step assay, the first step dilution assay, the second step assay, and the second step dilution assay are performed on the cartridge accommodation part 110 at the same time.

For example, in the first cartridge C1, a well W11 of the first column N1 may be an empty well into which the sample is injected, the piercer rincer may be stored in a well W12 of the second column N2, the piercer cleaner may be stored in a well W13 of the third column N3, the conjugate solution may be stored in a well W16 of the sixth column N6, the fixture solution may be stored in a well W17 of the seventh column N7, the cleaning solution may be stored in wells W19, W110, W111, and W112 of the ninth column N9 to the twelfth column N12, the pre-trigger solution may be stored in a well W117 of the seventeenth column N17, a trigger solution may be stored in a well W119 of the nineteenth column N19, which is provided as the well for the side light, and wells W14, W15, W18, W113, W114, W115, W116, and W118 of the fourth column N4, the fifth column N5, the eighth column N8, the thirteenth column N13 to the sixteenth column N16, and the eighteenth column N18 may be empty wells.

In the second cartridge C2, a well W21 of the first column N1 may be an empty well into which the sample is injected, the piercer rincer may be stored in a well W22 of the second column N2, the piercer cleaner may be stored in a well W23 of the third column N3, the diluent may be stored in a well W25 of the fifth column N5, the conjugate solution may be stored in a well W26 of the sixth column N6, the fixture solution may be stored in a well W27 of the seventh column N7, the cleaning solution may be stored in wells W29, W210, W211, and W212 of the ninth column N9 to the twelfth column N12, the pre-trigger solution may be stored in a well W217 of the seventeenth column N17, the trigger solution may be stored in a well W219 of the nineteenth column N19, which is provided as the well for the side light, and wells W24, W28, W213, W214, W215, W216, and W218 of the fourth column N4, the eighth column N8, the thirteenth column N13 to the sixteenth column N16, and the eighteenth column N18 may be empty wells.

In the third cartridge C3, a well W31 of the first column N1 may be an empty well into which the sample is injected, the piercer rincer may be stored in a well W32 of the second column N2, the piercer cleaner may be stored in a well W33 of the third column N3, the fixture solution may be may be stored in a well W37 of the seventh column N7, the conjugate solution stored in a well W38 of the eighth column N8, the cleaning solution may be stored in wells W39, W310, W311, W312, W313, W314, W315, and W316 of the ninth column N9 to the sixteenth column N16, the pre-trigger solution may be stored in a well W318 of the eighteenth column N18, the trigger solution may be stored in a well W319 of the nineteenth column N19, which is provided as the well for the side light, and wells W34, W35, W36, and W317 of the fourth column N4 to the sixth column N6 and the seventeenth column N17 may be empty wells.

In the fourth cartridge C4, a well W41 of the first column N1 may be an empty well into which the sample is injected, the piercer rincer may be stored in a well W42 of the second column N2, the piercer cleaner may be stored in a well W43 of the third column N3, the diluent may be stored in a well W45 of the fifth column N5, the fixture solution may be may be stored in a well W47 of the seventh column N7, the conjugate solution stored in a well W48 of the eighth column N8, the cleaning solution may be stored in wells W49, W410, W411, W412, W413, W414, W415, and W416 of the ninth column N9 to the sixteenth column N16, the pre-trigger solution may be stored in a well W418 of the eighteenth column N18, the trigger solution may be stored in a well W419 of the nineteenth column N19, which is provided as the well for the side light, and wells W44, W46, and W417 of the fourth column N4, the sixth column N6, and the seventeenth column N17 may be empty wells.

The above-described first to fourth cartridges C1 to C4 are disposed in the cartridge accommodation part 110, and the first step assay, the first step dilution assay, the second step assay, and the second step dilution assay may be performed on the cartridge accommodation part 110 at the same time. However, although only the four cartridges C1 to C4 are illustrated in the present embodiment, more cartridges may be disposed in the stage accommodation part 110 by combining the plurality of cartridges.

Before each reaction starts, a process of removing or punching a cartridge film may be performed. For example, the plurality of cartridges C1 to C4 are disposed in the first to fourth rows M1 to M4 of the cartridge accommodation part 110, and then, a punch part (not shown) punches films of the cartridges C1 to C4, which cover the cartridges, and a plurality of tips 210 are respectively mounted. After such a process, preparation of performing the reaction in each cartridge may be completed, and the four reactions described below may start in each cartridge C1 to C4 at the same time, respectively.

The first step assay using the first cartridge C1 is as follows (see FIG. 10).

A first tip 211 that moves relative to a stage 10 on the first row M1 suctions a sample (step S11) and then sequentially put in empty wells W15 and W14 (step S12) (here, simultaneously, a diluent is suctioned to perform dilution by each of the second tip 212 and the fourth tip 214 in the second cartridge C2 and the fourth cartridge C4), the simple is mixed with a conjugate solution stored in a well W16, and the mixed solution is suctioned again to the first tip 211 (step S13).

Thereafter, the mixed solution in the first tip 211 is discharged into a well W17 in which a fixture solution containing magnetic particles are stored and then mixed and cultured (step S14). Here, a lower end of the well W17 is surrounded by a heating block so that the culture process is performed at a temperature of about 37 degrees.

Thereafter, the first tip 211 suctions and discharges a cleaning solution stored in wells W19 to W112 to perform a cleaning process of removing impurities from the mixed solution except for a conjugate (conjugate of luminant-magnetic particle-biomarker) bonded to the magnetic particles (step S15). Particularly, in the cleaning process, the cleaning solution stored in a well W19 is suctioned into the first tip 211, and a magnetic force applying part 230 is attached around the first tip 211 to fix the magnetic particles inside the first tip 211. Then, a driving part 240 is driven to discharge only the impurities of the mixed solution within the first tip 211 together with the cleaning solution from the well W19. That is, only the impurities may be removed, but the conjugate bonded to the magnetic particles may remain in the first tip 211 through the cleaning process. This, the cleaning process may be repeated using the cleaning solution stored in the plurality of wells W19 to W112. Thereafter, the first tip 211 suctions the pre-trigger stored in the well 117 (step S16) to move to an upper side of a well W119 disposed at the outermost side of the cartridge. Then, when the solution within the first tip 211 is triggered onto the well W119, a luminant is measured by a measurement unit 300 moving to a side surface of the well W119 (step S17). Accordingly, the first step assay by the first tip 211 may be completed.

Thereafter, in order to complete the second step assay and the second step dilution assay of the third tip 213 and the fourth tip 214, the first tip 211 may stand by in the empty well W19 (the driving part 240 is not driven after being put in the empty well) (step S18) and then may sequentially stand by in the empty wells W113, W114, W115, and W116 (step S19), stand by in the empty well 118, and stand by in the empty well S119 (step S111).

In order to complete the second step assay and the second step dilution assay, which occur in the third tip 213 and the fourth tip 214, the above-described steps S18 to S111 are steps in which the first tip 211 dependently stands by in the empty well.

The second step dilution assay using the second cartridge C2 is as follows (see FIG. 11).

A second tip 212 moving relative to the stage 100 on the second row M2 suctions a sample (step S21) and then suctions a diluent stored in a well W25 to perform dilution of the simple in an empty well W24 (step S22). Thereafter, the diluted sample is mixed with a conjugate solution stored in a well W26 and then suctioned again to the first tip 211 (step S23).

Thereafter, the diluted sample in the second tip 212 is discharged into the well W27 in which a fixture solution containing magnetic particles are stored and then mixed and cultured (step S24). Likewise, a lower end of the well W27 is surrounded by a heating block so that the culture process is performed at a temperature of about 37 degrees.

Thereafter, the second tip 212 suctions and discharges a cleaning solution stored in wells W29 to W212 to perform a cleaning process of removing impurities from the mixed solution except for a magnetic particle conjugate (step S25).

Thereafter, the second tip 212 suctions the pre-trigger stored in the well 217 (step S26) to move to a well W219 disposed at the outermost side of the cartridge. Then, when the solution within the second tip 212 is triggered onto the well W219, a luminant is measured by a measurement unit 300 moving to a side surface of the well W219 (step S27). Accordingly, the second step dilution assay by the second tip 211 may be completed.

Thereafter, in order to complete the second step assay and the second step dilution assay of the third tip 213 and the fourth tip 214, the second tip 212 may stand by in an empty well W218 (the driving part 240 is not driven after being put in the empty well) (step S28) and then may sequentially stand by in the empty wells W213, W214, W215, and W216 (step S29), stand by in the empty well 218, and stand by in the empty well S218 (step S211).

In order to complete the second step assay and the second step dilution assay, which occur in the third tip 213 and the fourth tip 214, the above-described S28 to S211 are steps in which the second tip 212 dependently stands by in the empty well.

The second step assay using the third cartridge C4 is as follows (see FIG. 12).

A third tip 213 moving relative to the stage 100 on the third row M3 suctions a sample (step S31) and sequentially puts into empty wells W35 and W34 (step S32) and then puts again into an empty well W36 (step S33). (While the third cartridge C3 is placed in the empty wells W35 and W34, the dilution is performed at the same time after the diluent is suctioned from the second cartridge C2 and the fourth cartridge C4, and while the third cartridge C4 is paced in the empty well W36, the first cartridge C1 and the second cartridge C2 are mixed with the conjugate solution).

Thereafter, the simple in the third tip 213 is discharged into a well W37 in which a fixture solution containing magnetic particles are stored and then mixed and cultured (step S34). Here, a lower end of the well W37 is surrounded by a heating block so that the culture process is performed at a temperature of about 37 degrees.

Thereafter, the third tip 213 suctions and discharges a cleaning solution stored in wells W39 to W312 to perform a cleaning process of removing impurities from the mixed solution except for a magnetic particle conjugate (step S35).

Thereafter, the third tip 213 is put into the empty well W317 (step S36) and then stands by above a well W319 (step S37) (while the third cartridge C3 is placed in the empty well W317, the first cartridge C1 and the second cartridge C2 suction the pre-trigger, and while the third cartridge C3 stands by above the well W319, the solutions within the first cartridge C1 and the second cartridge C2 are triggered).

Thereafter, the mixed solution of the third tip 213 is mixed with the conjugate solution stored in the well W38 and then cultured (step S38).

Thereafter, the third tip 213 suctions and discharges a cleaning solution stored in wells W313 to W316 to perform a cleaning process of removing impurities from the mixed solution except for a magnetic particle conjugate (step S39).

Thereafter, the third tip 213 suctions the pre-trigger stored in the well 318 (step S310) to move to a well W319 disposed at the outermost side of the cartridge. Then, when the mixed solution within the third tip 213 is triggered onto the well W319, a luminant is measured by a measurement unit 300 moving to a side surface of the well W319 (step S311).

The second step dilution assay using the fourth cartridge C4 is as follows (see FIG. 13).

A fourth tip 214 moving relative to the stage 100 on the fourth row M4 suctions a sample (step S41) and then suctions a diluent stored in a well W45 to perform dilution of the simple in an empty well W44 (step S42).

Thereafter, the fourth tip 214 is put into the empty well W46 to stand by in the empty well W46 (step S43).

Thereafter, the simple in the fourth tip 214 is discharged into a well W47 in which a fixture solution containing magnetic particles are stored and then mixed and cultured (step S44). Here, a lower end of the well W47 is surrounded by a heating block so that the culture process is performed at a temperature of about 37 degrees.

Thereafter, the fourth tip 214 suctions and discharges a cleaning solution stored in wells W49 to W412 to perform a cleaning process of removing impurities from the mixed solution except for a magnetic particle conjugate (step S45).

Thereafter, the fourth tip 214 is put into the empty well W417 (step S46) and then stands by above a well W419 (step S47) (while the fourth cartridge C4 is placed in the empty well W417, the first cartridge C1 and the second cartridge C2 suction the pre-trigger, and while the fourth cartridge C4 stands by above the well W419, the solutions within the first cartridge C1 and the second cartridge C2 are triggered).

Thereafter, the mixed solution of the fourth tip 214 is mixed with the conjugate solution stored in the well W418 and then cultured (step S48).

Thereafter, the fourth tip 214 suctions and discharges a cleaning solution stored in wells W413 to W416 to perform a cleaning process of removing impurities from the mixed solution except for a magnetic particle conjugate (step S49).

Thereafter, the fourth tip 214 suctions the pre-trigger stored in the well 418 (step S410) to move to a well W419 disposed at the outermost side of the cartridge. Then, when the mixed solution within the fourth tip 214 is triggered onto the well W419, a luminant is measured by a measurement unit 300 moving to a side surface of the well W419 (step S411).

For the convenience of explanation, although each of the processes in which the first step assay, the first step dilution assay, the second step assay, and the second step dilution assay respectively occur on the cartridges, has been described, the reactions occur at the same time in the cartridge accommodation part 110 by the tips 210 that move at the same time and are independently adjusted in pressure by the driving part 240.

Particularly, the first tip 211 to the fourth tip 214 may move at the same time above the wells disposed in the same column N. That is, the above-described steps S11, S12, S31, and S41 occur at the same time, the above-described steps S12, S22, S32, and S42 occur at the same time, the above-described steps S13, S23, S33, and S43 occur at the same time, the above-described steps S14, S24, S34, and S44 occur at the same time, the above-described steps S15, S25, S35, and S45 occur at the same time, the above-described steps S16, S26, S36, and S46 occur at the same time, the above-described steps S17, S27, S37, and S47 occur at the same time, the above-described steps S18, S28, S38, and S48 occur at the same time, the above-described steps S19, S29, S39, and S49 occur at the same time, the above-described steps S110, S210, S310, and S410 occur at the same time, and the above-described steps S111, S211, S311, and S411 occur at the same time.

Also, the first cartridge C1 is disposed in the first row M1 of the cartridge accommodation part 110, the second cartridge C2 is disposed in the second row M2 of the cartridge accommodation part 110, the third cartridge C3 is disposed in the third row M3 of the cartridge accommodation part 110, and the fourth cartridge C4 is disposed in the fourth row M4 of the cartridge accommodation part unit 110, but each of the plurality of cartridges C1 to C4 may be disposed in any one of the plurality of rows M1 to M8 of the cartridge receiving unit 110. Thus, the order of the arrangement is not limited thereto.

The method in which at least two or more of the above-described first step assay, first step dilution assay, second step assay, and second step dilution assay occur on one stage may be understood as follows.

The step of performing the first step assay may include: a step (step S11) in which a first tip suctions a sample; a step (step S12) in which the first tip sequentially stands by in empty wells W15 and W14; a step (step S13) of suctioning a conjugate solution stored in a well W16; a step (step S14) of discharging a mixed solution stored in the first tip to a well W17, in which a fixture solution containing magnetic particles is stored, so as to be mixed and cultured; a cleaning step (step S15) in which the first tip suctions and discharges a cleaning solution stored in wells W19 to W112 to remove impurities except for a conjugate bonded to the magnetic particles; a step (step S16) in which the first tip suctions a pre-trigger stored in a well W117; a step (step S17) in which the first tip moves above a well W119 disposed at the outermost side of the cartridge to inject the solution stored in the first tip onto the well W119, thereby measuring the injected solution; a step (step S18) in which the first tip stands by in an empty well W118; a step (step S19) in which the first tip stands by in empty wells W113, W114, W115, and W116; a step (step S110) in which the first tip stands by in an empty well 118; and a step (step S111) in which the first tip stands by in an empty well S119.

The first step dilution assay may include: a step (step S21) in which a second tip suctions a sample; a step (step S22) in which the second tip suctions a diluent stored in a well W25 to dilute the sample in an empty well W24; a step (step S23) of mixing the diluted sample stored in the second tip with a conjugate solution stored in a well W26 to suction the mixed solution into the second tip; a step (step S24) of discharging the mixed solution stored in the second tip to a well W27, in which a fixture solution containing magnetic particles is stored, so as to be mixed and cultured; a cleaning step (step S25) in which the second tip suctions and discharges a cleaning solution stored in wells W29 to W212 to remove impurities from the mixed solution except for a magnetic particle conjugate; a step (step S26) in which the second tip suctions a pre-trigger stored in a well W217; a step (step S27) in which the second tip moves to a well W219 disposed at the outermost side of the cartridge to inject the solution stored in the second tip onto the well W219, thereby measuring the injected solution; a step (step S28) in which the second tip stands by in an empty well W218; a step (step S29) in which the second tip stands by in empty wells W213, W214, W215, and W216; a step (step S210) in which the second tip stands by in an empty well 218; and a step (step S211) in which the second tip stands by in an empty well S218, and The second step assay may include: a step (step S31) in which a third tip suctions a sample; a step (step S32) in which the third tip sequentially stands by in empty wells W35 and W34; a step (step S33) in which the third tip stands by in an empty well W36; a step (step S34) of discharging the sample stored in the third tip to a well W37, in which a fixture solution containing magnetic particles is stored, so as to be mixed and cultured; a cleaning step (step S35) of suctioning and discharging a cleaning solution stored in wells W39 to W312 to remove impurities from the mixed solution except for a magnetic particle conjugate; a step (step S36) in which the third chip stands by in an empty W317; a step (step S37) in which the third tip stands by above an well W319; a step (step S38) in which the mixed solution of the third tip is mixed with the conjugate solution stored in a well W38 so as to be cultured; a step (step S39) in which the third tip suctions and discharges a cleaning solution stored in wells W313 to W316 to remove impurities from the mixed solution except for a magnetic particle conjugate; a step (step S310) in which the third tip suctions a pre-trigger stored in a well W317; and a step (step S311) in which the third tip moves to a well W319 disposed at the outermost side of the cartridge to inject the mixed solution onto the well W319, thereby measuring the injected solution, and the second step dilution assay includes: a step (step S41) in which a fourth tip suctions a sample; a step (step S42) in which the fourth tip suctions a diluent stored in a well W45 to dilute the sample in an empty well W44; a step (step S43) in which the fourth tip stands by in an empty well W46; a step (step S44) of discharging the diluted sample stored in the second tip to a well W47, in which a fixture solution containing magnetic particles is stored, so as to be mixed and cultured; a cleaning step (step S45) in which the fourth tip suctions and discharges a cleaning solution stored in wells W49 to W412 to remove impurities from the mixed solution except for a magnetic particle conjugate; a step (step S46) in which the fourth tip stands by in an empty well W417; a step (step S47) in which the fourth tip stands by above an empty well W419; a step (step S48) in which a mixed solution of the fourth tip is mixed with a conjugate solution stored in an well W48 so as to be cultured; a step (step S410) in which the fourth tip suctions a pre-trigger stored in a well W418; and a step (step S411) in which the fourth tip moves to a well W419 disposed at the outermost side of the cartridge to inject the mixed solution onto the well W419, thereby measuring the injected solution. Here, at least two reactions of the first step assay, the first step dilution assay, the second step assay, and the second step dilution assay may occur on one stage at the same time. Also, according to an embodiment of the present invention, the second step assay may include: a step in which at least two tips (e.g., a first tip and a third tip) of a plurality of tips suction samples different from each other, respectively; a step in which at least one tip (e.g., the first tip) of the plurality of tips, which suctions the sample, suctions a conjugate solution, and at least the other tip (e.g., the third tip) stands by in an empty well; a step in which the plurality of tips (e.g., the first tip and the third tip), into which the sample is suctioned, discharge a contents stored in the tip to a well containing a fixture solution so as to be mixed and cultured; a cleaning step in which the plurality of tips (e.g., the first tip and the third tip) suctioning the sample suction and discharge a cleaning solution to remove impurities except for a magnetic particle conjugate; a step in which at least one tip (e.g., the first tip) suctioning the conjugate solution suctions a pre-trigger, and at least the other tip (e.g., the third tip) stands by above an empty well; a step in which at least one tip (e.g., the first tip) suctioning the pre-trigger injects the content contained in the tip onto a well to measure the injected solution by using a measurement unit, and at least the other tip (e.g., the third tip) stands by above an empty well; a step in which at least one tip (e.g., the first tip) injecting the content contained in the tip onto the well stands by in an empty well, and at least the other tip (e.g., the third tip) suctions a conjugate solution; a cleaning step in which at least one tip (e.g., the first tip) injecting the content contained in the tip onto the well stands by in an empty well, and at least the other tip (e.g., the third tip) suctions and discharges the cleaning solution to remove impurities except for a magnetic particle conjugate; a step in which at least one tip (e.g., the first tip) injecting the content contained in the tip onto the well stands by in an empty well, and at least the other tip (e.g., the third tip) suctions the pre-trigger; and a step in which at least one tip (e.g., the first tip) injecting the content contained in the tip onto the well stands by above the well, and at least the other tip (e.g., the third tip) injects the content contained in the tip onto the well to measure the injected solution by using a measurement unit.

Also, a step in which at least one (e.g., the second tip and the fourth tip) of the plurality of tips suctions a diluent before suctioning the conjugate solution and the fixture solution to dilute the sample in the empty well may be further performed.

Also, according to an aspect of the present invention, the immunoassay method may include a step in which at least the other tip stands by above an empty well while at least one tip of a plurality of tips suctions a solution stored in a well or discharges the suctioned solution from the well so that a plurality of reaction methods are performed on one state at the same time.

Also, according to an aspect of the present invention, the plurality of reaction methods may include two or more assays of a first step assay, a first step dilution assay, a second step assay, and a second step dilution assay.

Also, according to an aspect of the present invention, the plurality of reaction methods may include a first step assay and a second step assay, and the immunoassay method may further include: a step in which the tip for performing the second step assay stands by above the empty well while the tip for performing the first step assay suctions a conjugate solution; and a step in which the tip for performing the first step assay stands by above the empty well while the tip for performing the second step assay suctions the conjugate solution.

Also, according to an aspect of the present invention, the immunoassay method may further include: a step in which the tip for performing the second step assay stands by above the empty well while the tip for performing the first step assay suctions a pre-trigger solution; and a step in which the tip for performing the first step assay stands by above the empty well while the tip for performing the second step assay suctions the pre-trigger solution.

Also, according to an aspect of the present invention, the immunoassay method may further include: a step in which the tip for performing the second step assay stands by above the empty well while the solution stored in the tip for performing the first step assay is measured by a measurement unit; and a step in which the tip for performing the first step assay stands by above the empty well while the solution stored in the tip for performing the second step assay is measured by the measurement unit.

Also, according to an aspect of the present invention, at least one assay of the first step assay and the second assay may additionally include a step of diluting a sample, and the immunoassay method may further include a step in which the other tip stands by above the empty well while the tip for performing the first step assay or the tip for performing the second step assay suctions a diluent.

Also, according to an aspect of the present invention, the plurality of reaction methods may include a first step assay and a first step dilution assay, and the immunoassay method may further include: a step in which the tip for performing the first step assay stands by above the empty well while the tip for performing the first step dilution assay suctions the diluent.

Also, according to an aspect of the present invention, the plurality of reaction methods may include a second step assay and a second step dilution assay, and the immunoassay method may further include: a step in which the tip for performing the second step assay stands by above the empty well while the tip for performing the second step dilution assay suctions the diluent.

Also, according to an aspect of the present invention, a change in pressure within the tip that stands by above the empty well may not occur.

Hereinafter, operations and effects of an immunoassay device and immunoassay method according to an embodiment of the present invention will be described.

The immunoassay device according to the embodiment of the present invention may perform various reaction methods on one stage.

Also, a plurality of cartridges C may respectively include a plurality of reagents and be disposed to be provided with at least two empty wells (each of a first cartridge C1 and a second cartridge C2 includes seven empty wells (except for an empty well for storing a sample), and a third cartridge C3 and a fourth cartridge C4 includes four empty wells), and thus, a plurality of reaction methods may be performed on a stage at the same time.

Also, the plurality of cartridges C may be arranged so that at least one of arrangements of columns of the wells in which a conjugate solution and a pre-trigger solution are stored is different, and arrangements of columns of wells in which a fixture solution is stored are the same, and thus, the plurality of reaction methods may be performed on the stage at the same time.

Also, since a driving part 240 independently applies a pressure to each of tips 210, the plurality of reaction methods may be smoothly performed on one stage 100.

Also, since a magnet apply part 230 is provided on a side surface of a tip 210, magnetic particles may be maintained or fixed in the tip to improve precision of a reaction test.

Also, since the magnet 232 and the tip 210 are fitted with respect to each other, magnetic force applied to the magnetic particles inside the tip 210 may be constantly adjusted.

Also, since a moving measurement unit 300 is provided, reaction and measurement of the sample may occur on one stage to reduce an inspection time.

Also, a well disposed at the outermost side may measure a luminant by the measurement unit 300 that is provided to form a darkroom.

Also, an accurate measurement device for flash type measurement as a small device may be provided.

The device and the immunoassay method according to the embodiment of the present invention have been described above as specific embodiments, but these are merely examples, and thus, the present invention is not limited thereto. It should be construed as having the broadest scope according to the basic idea disclosed herein. Those skilled in the art may combine and replace the disclosed embodiments to implement patterns in a shape that is not described, but this is also within the scope of the present invention. In addition, those skilled in the art may easily change or modify the disclosed embodiments based on the present specification, and it is obvious that such changes or modifications fall within the scope of the present invention.

The invention claimed is:

1. An immunoassay device comprising:
   a stage configured to accommodate a plurality of cartridges, each cartridge of the plurality of cartridges having a plurality of wells that are opened upward, wherein the stage is configured to surround a circumference of the well disposed at the outermost side of the cartridges;
   a solution transfer unit comprising a plurality of tips that are configured to move relative to the stage, are disposed to correspond to positions of the each cartridge, and configured to suction a solution stored in the wells or discharge the suctioned solution from the wells; and
   a measurement unit disposed at one side of the stage to move in a direction in which the plurality of cartridges are arranged, and comprising a detection unit for measuring an inside state of the well disposed at the outermost side of the each cartridge, and a shielding plate configured to move to cover an opened upper portion of the well disposed at the outermost side of the each cartridge to block introduction of light into the well,
   wherein a hole through which an end of a tip of the plurality of tips is introduced into an upper portion of the well disposed at the outermost side of the cartridges, is provided in the shielding plate,
   the hole of the shielding plate has a size less than that of an upper hole of the well disposed at the outermost side of the cartridges, and
   when the tip of the plurality of tips is introduced into the well disposed at the outermost side of the cartridges, light incident into the well through a second hole of the shielding plate is blocked.

2. The immunoassay device of claim 1, wherein a first hole for measuring a state of the solution is provided in one side surface of the stage that surrounds the circumference of the well disposed at the outermost side of the cartridges,
   the detection unit is provided on one side surface of the measurement unit; and
   when the detection unit is disposed on the side surface of the well disposed at the outermost side of the cartridges to measure the state of the solution, the light incident into the well through the first hole is blocked.

3. An immunoassay device comprising:
   a stage configured to accommodate a plurality of cartridges, each cartridge of the plurality of cartridges having a plurality of wells that are opened upward, wherein the stage is configured to surround a circumference of the well disposed at the outermost side of the cartridges;
   a solution transfer unit comprising a plurality of tips that are configured to move relative to the stage, are disposed to correspond to positions of the each cartridge, and configured to suction a solution stored in the wells or discharge the suctioned solution from the wells; and
   a measurement unit disposed at one side of the stage to move in a direction in which the plurality of cartridges are arranged, and comprising a detection unit for measuring an inside state of the well disposed at the outermost side of the each cartridge, and a shielding plate configured to move to cover an opened upper portion of the well disposed at the outermost side of the each cartridge to block introduction of light into the well,
   wherein the detection unit and a hole formed in the shielding plate are provided in plurality to measure states of the solutions stored in the plurality of wells disposed at the outermost side of the cartridges at the same time.

4. The immunoassay device of claim 1, wherein the solution transfer unit comprises a magnetic force applying part that is capable of applying magnetic force toward the tip, and
   when the solution stored in the tip is injected into the well disposed at the outermost side of the cartridges, the magnetic force applying part approaches the tip, and magnetic particles are held inside the tip.

5. The immunoassay device of claim 1, further comprising a measurement unit driving part that is capable of driving the measurement unit in at least one direction,
   wherein the measurement unit is reciprocated along the wells, which are disposed at the outermost side of the cartridges.

* * * * *